(12) United States Patent
Roschak et al.

(10) Patent No.: US 12,329,374 B2
(45) Date of Patent: *Jun. 17, 2025

(54) NONINVASIVELY ADJUSTABLE SUTURE ANCHORS

(71) Applicant: NuVasive Specialized Orthopedics, Inc., San Diego, CA (US)

(72) Inventors: Edmund J. Roschak, Mission Viejo, CA (US); Thomas B. Buford, Laguna Beach, CA (US); Blair Walker, Mission Viejo, CA (US)

(73) Assignee: Nuvasive Specialized Orthopedics Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/233,472

(22) Filed: Aug. 14, 2023

(65) Prior Publication Data
US 2023/0380830 A1 Nov. 30, 2023

Related U.S. Application Data

(60) Continuation of application No. 17/374,350, filed on Jul. 13, 2021, now Pat. No. 11,766,252, which is a
(Continued)

(51) Int. Cl.
*A61B 17/04* (2006.01)
*A61B 17/00* (2006.01)

(52) U.S. Cl.
CPC ............... *A61B 17/0401* (2013.01); *A61B 2017/00876* (2013.01); *A61B 2017/0409* (2013.01);
(Continued)

(58) Field of Classification Search
CPC ............ A61B 17/86–8695; A61B 17/04–0493
(Continued)

(56) References Cited

U.S. PATENT DOCUMENTS

| 2,702,031 | A | 2/1955 | Wenger |
| 3,111,945 | A | 11/1963 | Von Solbrig |

(Continued)

FOREIGN PATENT DOCUMENTS

| CN | 1697630 A | 11/2005 |
| CN | 101040807 A | 9/2007 |

(Continued)

OTHER PUBLICATIONS

Abe et al., "Experimental external fixation combined with percutaneous discectomy in the management of scoliosis.", Spine, 1999, pp. 646-653, 24, No. 7.
(Continued)

*Primary Examiner* — Matthew J Lawson

(57) ABSTRACT

In one embodiment, a method of treating a patient includes: providing a tensioning device having: a connector configured to couple to a soft tissue, and an adjustable anchor configured to couple to the connector and to couple to a bone, wherein the adjustable anchor comprises: a first end and a second end; a housing extending between the first end and the second end; and an adjustable component disposed within the housing; inserting the second end of the adjustable anchor into the bone; connecting the connector to the soft tissue; coupling the connector to the adjustable anchor; and adjusting a tension on the connector by rotating the adjustable component within the housing in response to a wireless signal.

11 Claims, 10 Drawing Sheets

Related U.S. Application Data division of application No. 16/257,526, filed on Jan. 25, 2019, now Pat. No. 11,090,039, which is a continuation of application No. 14/447,391, filed on Jul. 30, 2014, now Pat. No. 10,226,242.

(60) Provisional application No. 61/860,668, filed on Jul. 31, 2013.

(52) U.S. Cl.
CPC .................. *A61B 2017/0414* (2013.01); *A61B 2017/044* (2013.01); *A61B 2017/0453* (2013.01); *A61B 2017/0458* (2013.01)

(58) Field of Classification Search
USPC ......... 623/13.11–13.2; 606/62–68, 246–279, 606/300–321
See application file for complete search history.

(56) References Cited

U.S. PATENT DOCUMENTS

| | | |
|---|---|---|
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |

(56) References Cited

U.S. PATENT DOCUMENTS

| | | |
|---|---|---|
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,674,276 B2 | 3/2010 | Stone et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |

(56) References Cited

U.S. PATENT DOCUMENTS

| | | | |
|---|---|---|---|
| 8,556,975 B2 | 10/2013 | Ciupik et al. | |
| 8,562,653 B2 | 10/2013 | Alamin et al. | |
| 8,568,457 B2 | 10/2013 | Hunziker | |
| 8,617,220 B2 | 10/2013 | Skaggs | |
| 8,579,979 B2 | 11/2013 | Edie et al. | |
| 8,585,595 B2 | 11/2013 | Heilman | |
| 8,585,740 B1 | 11/2013 | Ross et al. | |
| 8,591,549 B2 | 11/2013 | Lange | |
| 8,591,553 B2 | 11/2013 | Eisermann et al. | |
| 8,613,758 B2 | 12/2013 | Linares | |
| 8,623,036 B2 | 1/2014 | Harrison et al. | |
| 8,632,544 B2 | 1/2014 | Haaja et al. | |
| 8,632,548 B2 | 1/2014 | Soubeiran | |
| 8,632,563 B2 | 1/2014 | Nagase et al. | |
| 8,636,771 B2 | 1/2014 | Butler et al. | |
| 8,636,802 B2 | 1/2014 | Serhan et al. | |
| 8,641,719 B2 | 2/2014 | Gephart et al. | |
| 8,641,723 B2 | 2/2014 | Connor | |
| 8,657,856 B2 | 2/2014 | Gephart et al. | |
| 8,663,285 B2 | 3/2014 | Dall et al. | |
| 8,663,287 B2 | 3/2014 | Butler et al. | |
| 8,668,719 B2 | 3/2014 | Alamin et al. | |
| 8,709,090 B2 | 4/2014 | Makower et al. | |
| 8,758,347 B2 | 6/2014 | Weiner et al. | |
| 8,758,355 B2 | 6/2014 | Fisher et al. | |
| 8,771,272 B2 | 7/2014 | LeCronier et al. | |
| 8,777,947 B2 | 7/2014 | Zahrly et al. | |
| 8,777,990 B2 * | 7/2014 | van der Burg | A61B 17/0401 606/232 |
| 8,777,995 B2 | 7/2014 | McClintock et al. | |
| 8,790,343 B2 | 7/2014 | McClellan et al. | |
| 8,790,409 B2 | 7/2014 | Van den Heuvel et al. | |
| 8,828,058 B2 | 9/2014 | Elsebaie et al. | |
| 8,828,087 B2 | 9/2014 | Stone et al. | |
| 8,840,651 B2 | 9/2014 | Reiley | |
| 8,870,881 B2 | 10/2014 | Rezach et al. | |
| 8,870,959 B2 | 10/2014 | Arnin | |
| 8,915,915 B2 | 12/2014 | Harrison et al. | |
| 8,915,917 B2 | 12/2014 | Doherty et al. | |
| 8,920,422 B2 | 12/2014 | Homeier et al. | |
| 8,945,188 B2 | 2/2015 | Rezach et al. | |
| 8,961,521 B2 | 2/2015 | Keefer et al. | |
| 8,961,567 B2 | 2/2015 | Hunziker | |
| 8,968,402 B2 | 3/2015 | Myers et al. | |
| 8,992,527 B2 | 3/2015 | Guichet | |
| 9,022,917 B2 | 5/2015 | Kasic et al. | |
| 9,044,218 B2 | 6/2015 | Young | |
| 9,060,810 B2 | 6/2015 | Kercher et al. | |
| 9,078,703 B2 | 7/2015 | Arnin | |
| 10,226,242 B2 | 3/2019 | Roschak et al. | |
| 11,918,264 B2 * | 3/2024 | Conley | A61F 2/0811 |
| 2002/0050112 A1 | 5/2002 | Koch et al. | |
| 2002/0072758 A1 | 6/2002 | Reo et al. | |
| 2002/0164905 A1 | 11/2002 | Bryant | |
| 2003/0040671 A1 | 2/2003 | Somogyi et al. | |
| 2003/0144669 A1 | 7/2003 | Robinson | |
| 2003/0220643 A1 | 11/2003 | Ferree | |
| 2003/0220644 A1 | 11/2003 | Thelen et al. | |
| 2004/0011137 A1 | 1/2004 | Hnat et al. | |
| 2004/0011365 A1 | 1/2004 | Govari et al. | |
| 2004/0019353 A1 | 1/2004 | Freid et al. | |
| 2004/0023623 A1 | 2/2004 | Stauch et al. | |
| 2004/0055610 A1 | 3/2004 | Forsell | |
| 2004/0133219 A1 | 7/2004 | Forsell | |
| 2004/0138725 A1 | 7/2004 | Forsell | |
| 2004/0193266 A1 | 9/2004 | Meyer | |
| 2005/0034705 A1 | 2/2005 | McClendon | |
| 2005/0049617 A1 | 3/2005 | Chatlynne et al. | |
| 2005/0065529 A1 | 3/2005 | Liu et al. | |
| 2005/0090823 A1 | 4/2005 | Bartimus | |
| 2005/0159754 A1 | 7/2005 | Odrich | |
| 2005/0234448 A1 | 10/2005 | McCarthy | |
| 2005/0234462 A1 | 10/2005 | Hershberger | |
| 2005/0246034 A1 | 11/2005 | Soubeiran | |
| 2005/0261779 A1 | 11/2005 | Meyer | |
| 2005/0272976 A1 | 12/2005 | Tanaka et al. | |
| 2006/0004459 A1 | 1/2006 | Hazebrouck et al. | |
| 2006/0009767 A1 | 1/2006 | Kiester | |
| 2006/0036259 A1 | 2/2006 | Carl et al. | |
| 2006/0036323 A1 | 2/2006 | Carl et al. | |
| 2006/0036324 A1 | 2/2006 | Sachs et al. | |
| 2006/0047282 A1 * | 3/2006 | Gordon | A61B 17/7016 606/907 |
| 2006/0058792 A1 | 3/2006 | Hynes | |
| 2006/0069447 A1 | 3/2006 | DiSilvestro et al. | |
| 2006/0074448 A1 | 4/2006 | Harrison et al. | |
| 2006/0079897 A1 | 4/2006 | Harrison et al. | |
| 2006/0136062 A1 | 6/2006 | DiNello et al. | |
| 2006/0142767 A1 | 6/2006 | Green et al. | |
| 2006/0155279 A1 | 7/2006 | Ogilvie | |
| 2006/0195087 A1 | 8/2006 | Sacher et al. | |
| 2006/0195088 A1 | 8/2006 | Sacher et al. | |
| 2006/0200134 A1 | 9/2006 | Freid et al. | |
| 2006/0204156 A1 | 9/2006 | Takehara et al. | |
| 2006/0235299 A1 | 10/2006 | Martinelli | |
| 2006/0235424 A1 | 10/2006 | Vitale et al. | |
| 2006/0241746 A1 | 10/2006 | Shaoulian et al. | |
| 2006/0241767 A1 | 10/2006 | Doty | |
| 2006/0249914 A1 | 11/2006 | Dulin | |
| 2006/0271107 A1 | 11/2006 | Harrison et al. | |
| 2006/0282073 A1 | 12/2006 | Simanovsky | |
| 2006/0293683 A1 | 12/2006 | Stauch | |
| 2007/0010814 A1 | 1/2007 | Stauch | |
| 2007/0010887 A1 | 1/2007 | Williams et al. | |
| 2007/0021644 A1 | 1/2007 | Woolson et al. | |
| 2007/0031131 A1 | 2/2007 | Griffitts | |
| 2007/0043376 A1 | 2/2007 | Leatherbury et al. | |
| 2007/0050030 A1 | 3/2007 | Kim | |
| 2007/0118215 A1 | 5/2007 | Moaddeb | |
| 2007/0161984 A1 | 7/2007 | Cresina et al. | |
| 2007/0173837 A1 | 7/2007 | Chan et al. | |
| 2007/0179493 A1 | 8/2007 | Kim | |
| 2007/0185374 A1 | 8/2007 | Kick et al. | |
| 2007/0233098 A1 | 10/2007 | Mastrorio et al. | |
| 2007/0239159 A1 | 10/2007 | Altarac et al. | |
| 2007/0239161 A1 | 10/2007 | Giger et al. | |
| 2007/0255088 A1 | 11/2007 | Jacobson et al. | |
| 2007/0270803 A1 | 11/2007 | Giger et al. | |
| 2007/0276368 A1 | 11/2007 | Trieu et al. | |
| 2007/0276369 A1 | 11/2007 | Allard et al. | |
| 2007/0276373 A1 | 11/2007 | Malandain | |
| 2007/0276378 A1 | 11/2007 | Harrison et al. | |
| 2007/0276493 A1 | 11/2007 | Malandain et al. | |
| 2007/0288024 A1 | 12/2007 | Gollogly | |
| 2007/0288183 A1 | 12/2007 | Bulkes et al. | |
| 2008/0009792 A1 | 1/2008 | Henniges et al. | |
| 2008/0015577 A1 | 1/2008 | Loeb | |
| 2008/0021454 A1 | 1/2008 | Chao et al. | |
| 2008/0021455 A1 | 1/2008 | Chao et al. | |
| 2008/0021456 A1 | 1/2008 | Gupta et al. | |
| 2008/0027436 A1 | 1/2008 | Cournoyer et al. | |
| 2008/0033431 A1 | 2/2008 | Jung et al. | |
| 2008/0033436 A1 | 2/2008 | Song et al. | |
| 2008/0051784 A1 | 2/2008 | Gollogly | |
| 2008/0082118 A1 | 4/2008 | Edidin et al. | |
| 2008/0086128 A1 | 4/2008 | Lewis | |
| 2008/0097487 A1 | 4/2008 | Pool et al. | |
| 2008/0097496 A1 | 4/2008 | Chang et al. | |
| 2008/0108995 A1 | 5/2008 | Conway et al. | |
| 2008/0161933 A1 | 7/2008 | Grotz et al. | |
| 2008/0167685 A1 | 7/2008 | Allard et al. | |
| 2008/0172063 A1 | 7/2008 | Taylor | |
| 2008/0177319 A1 | 7/2008 | Schwab | |
| 2008/0177326 A1 | 7/2008 | Thompson | |
| 2008/0190237 A1 | 8/2008 | Radinger et al. | |
| 2008/0228186 A1 | 9/2008 | Gall et al. | |
| 2008/0255615 A1 | 10/2008 | Vittur et al. | |
| 2008/0272928 A1 | 11/2008 | Shuster | |
| 2008/0275557 A1 | 11/2008 | Makower et al. | |
| 2009/0030462 A1 | 1/2009 | Buttermann | |
| 2009/0043337 A1 * | 2/2009 | Martin | A61B 17/0401 606/301 |
| 2009/0076597 A1 | 3/2009 | Dahlgren et al. | |
| 2009/0082815 A1 | 3/2009 | Zylber et al. | |

(56) References Cited

U.S. PATENT DOCUMENTS

| | | |
|---|---|---|
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112207 A1 | 4/2009 | Walker et al. |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0245088 A1 | 10/2009 | Takeuchi et al. |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0063542 A1 | 3/2010 | van der Burg et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0249837 A1 | 9/2010 | Seme et al. |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0060336 A1 | 3/2011 | Pool et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0230883 A1* | 9/2011 | Zahrly ............... A61B 17/7225 606/63 |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0190871 A1* | 7/2013 | Markarian ......... A61B 17/0401 623/13.13 |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128868 A1 | 5/2014 | Harrison et al. |
| 2014/0128920 A1 | 5/2014 | Kantelhardt |
| 2014/0163664 A1 | 6/2014 | Goldsmith |
| 2014/0181234 A1 | 6/2014 | Hsiao et al. |
| 2014/0214034 A1 | 7/2014 | Rayes et al. |
| 2014/0228880 A1 | 8/2014 | Bisson et al. |
| 2014/0236234 A1* | 8/2014 | Kroll ................. A61B 17/7083 606/279 |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0296919 A1* | 10/2014 | Culbert ............. A61B 17/7037 606/272 |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |
| 2015/0313745 A1 | 11/2015 | Cheng |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 12/2011 |
| JP | H0956736 | 3/1997 |
| JP | 2002500063 A | 1/2002 |
| WO | WO1998044858 A1 | 10/1998 |
| WO | WO1999051160 A1 | 10/1999 |
| WO | WO2001024697 A1 | 4/2001 |
| WO | WO2001045485 A3 | 6/2001 |
| WO | WO2001045487 A2 | 6/2001 |
| WO | WO2001067973 A2 | 9/2001 |
| WO | WO2001078614 A1 | 10/2001 |
| WO | WO2007013059 A3 | 2/2007 |
| WO | WO2007015239 A3 | 2/2007 |
| WO | WO2011116158 A3 | 9/2011 |
| WO | WO2013119528 A1 | 8/2013 |
| WO | WO2014040013 A1 | 3/2014 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

(56) References Cited

OTHER PUBLICATIONS

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

Dorsey et al., "The stability of three commercially available implants used in medial opening wedge high tibial osteotomy.", Journal of Knee Surgery, 2006, pp. 95-98, 19, No. 2.

Edeland et al., "Instrumentation for distraction by limited surgery in scoliosis treatment.", Journal of Biomedical Engineering, 1981, pp. 143-146, 3, No. 2.

Elsebaie, "Single growing rods (Review of 21 cases). Changing the foundations: Does it affect the results?", Journal of Child Orthop, 2007, 1:258.

Ember et al., "Distraction forces required during growth rod lengthening.", J of Bone Joint Surg BR, 2006, p. 229, 88-B, No. Suppl. II.

European Patent Office, "Observations by a third party under Article 115 EPC in EP08805612 by Soubeiran.", 2010.

Fabry et al., "A technique for prevention of port complications after laparoscopic adjustable silicone gastric banding.", Obesity Surgery, 2002, pp. 285-288, 12, No. 2.

Fried et al., "In vivo measurements of different gastric band pressures towards the gastric wall at the stoma region.", Obesity Surgery, 2004, p. 914, 14, No. 7.

Gao et al., CHD7 gene polymorphisms are associated with susceptibility to idiopathic scoliosis, American Journal of Human Genetics, 2007, pp. 957-965, 80.

Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).

Gillespie et al. "Harrington instrumentation without fusion.", J Bone Joint Surg Br, 1981, p. 461, 63-B, No. 3.

Goodship et al., "Strain rate and timing of stimulation in mechanical modulation of fracture healing.", Clinical Orthopaedics and Related Research, 1998, pp. S105-S115, No. 355S.

Grass et al., "Intermittent distracting rod for correction of high neurologic risk congenital scoliosis.", Spine, 1997, pp. 1922-1927, 22, No. 16.

Gray, "Gray's anatomy of the human body.", http://education.yahoo.com/reference/gray/subjects/subject/128, published Jul. 1, 2007.

Grimer et al. "Non-invasive extendable endoprostheses for children— Expensive but worth it!", International Society of Limb Salvage 14th International Symposium on Limb Salvage, 2007.

Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.

Guichet et al. "Gradual femoral lengthening with the Albizzia intramedullary nail", J Bone Joint Surg Am, 2003, pp. 838-848, 85-A, No. 5.

Gupta et al., "Non-invasive distal femoral expandable endoprosthesis for limb-salvage surgery in paediatric tumours.", J Bone Joint Surg Br, 2006, pp. 649-654, 88-B, No. 5.

Hankemeier et al., "Limb lengthening with the Intramedullary Skeletal Kinetic Distractor (ISKD).", Oper Orthop Traumatol, 2005, pp. 79-101, 17, No. 1.

Harrington, "Treatment of scoliosis. Correction and internal fixation by spine instrumentation.", J Bone Joint Surg Am, 1962, pp. 591-610, 44-A, No. 4.

Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.

Hofmeister et al., "Callus distraction with the Albizzia nail.", Practice of Intramedullary Locked Nails, 2006, pp. 211-215.

Horbach et al., "First experiences with the routine use of the Rapid Port™ system with the Lap-Band®.", Obesity Surgery, 2006, p. 418, 16, No. 4.

Hyodo et al., "Bone transport using intramedullary fixation and a single flexible traction cable.", Clinical Orthopaedics and Related Research, 1996, pp. 256-268, 325.

International Commission on Non-Ionizing Radiation Protection, "Guidelines on limits of exposure to static magnetic fields." Health Physics, 2009, pp. 504-514, 96, No. 4.

INVIS®/Lamello Catalog, 2006, Article No. 68906A001 GB.

Kasliwal et al., "Management of high-grade spondylolisthesis.", Neurosurgery Clinics of North America, 2013, pp. 275-291, 24, No. 2.

Kenawey et al., "Leg lengthening using intramedullay skeletal kinetic distractor: Results of 57 consecutive applications.", Injury, 2011, pp. 150-155, 42, No. 2.

Kent et al., "Assessment and correction of femoral malrotation following intramedullary nailing of the femur.", Acta Orthop Belg, 2010, pp. 580-584, 76, No. 5.

Klemme et al., "Spinal instrumentation without fusion for progressive scoliosis in young children", Journal of Pediatric Orthopaedics. 1997, pp. 734-742, 17, No. 6.

Korenkov et al., "Port function after laparoscopic adjustable gastric banding for morbid obesity.", Surgical Endoscopy, 2003, pp. 1068-1071, 17, No. 7.

Krieg et al., "Leg lengthening with a motorized nail in adolescents.", Clinical Orthopaedics and Related Research, 2008, pp. 189-197, 466, No. 1.

Kucukkaya et al., "The new intramedullary cable bone transport technique.", Journal of Orthopaedic Trauma, 2009, pp. 531-536, 23, No. 7.

Lechner et al., "In vivo band manometry: A new method in band adjustment", Obesity Surgery, 2005, p. 935, 15, No. 7.

Lechner et al., "Intra-band manometry for band adjustments: The basics", Obesity Surgery, 2006, pp. 417-418, 16, No. 4.

Li et al., "Bone transport over an intramedullary nail: A case report with histologic examination of the regenerated segment.", Injury, 1999, pp. 525-534, 30, No. 8.

(56) References Cited

OTHER PUBLICATIONS

Lonner, "Emerging minimally invasive technologies for the management of scoliosis.", Orthopedic Clinics of North America, 2007, pp. 431-440, 38, No. 3.

Matthews et al., "Magnetically adjustable intraocular lens.", Journal of Cataract and Refractive Surgery, 2003, pp. 2211-2216, 29, No. 11.

MicroMotion, "Micro Drive Engineering. General catalogue.", 2009, pp. 14-24.

Mineiro et al., "Subcutaneous rodding for progressive spinal curvatures: Early results.", Journal of Pediatric Orthopaedics, 2002, pp. 290-295, 22, No. 3.

Moe et al., "Harrington instrumentation without fusion plus external orthotic support for the treatment of difficult curvature problems in young children.", Clinical Orthopaedics and Related Research, 1984, pp. 35-45, 185.

Montague et al., "Magnetic gear dynamics for servo control.", Melecon 2010-2010 15th IEEE Mediterranean Electrotechnical Conference, Valletta, 2010, pp. 1192-1197.

Montague et al., "Servo control of magnetic gears.", IEEE/ASME Transactions on Mechatronics, 2012, pp. 269-278, 17, No. 2.

Nachemson et al., "Intravital wireless telemetry of axial forces in Harrington distraction rods in patients with idiopathic scoliosis.", The Journal of Bone and Joint Surgery, 1971, pp. 445-465, 53, No. 3.

Nachlas et al., "The cure of experimental scoliosis by directed growth control.", The Journal of Bone and Joint Surgery, 1951, pp. 24-34, 33-A, No. 1.

Newton et al., "Fusionless scoliosis correction by anterolateral tethering . . . can it work?.", 39th Annual Scoliosis Research Society Meeting, 2004.

Oh et al., "Bone transport over an intramedullary nail for reconstruction of long bone defects in tibia.", Archives of Orthopaedic and Trauma Surgery, 2008, pp. 801-808, 128, No. 8.

Ozcivici et al., "Mechanical signals as anabolic agents in bone.", Nature Reviews Rheumatology, 2010, pp. 50-59, 6, No. 1.

Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.

Prontes, "Longest bone in body.", eHow.com, 2012.

Rathjen et al., "Clinical and radiographic results after implant removal in idiopathic scoliosis.", Spine, 2007, pp. 2184-2188, 32, No. 20.

Ren et al., "Laparoscopic adjustable gastric banding: Surgical technique", Journal of Laparoendoscopic & Advanced Surgical Techniques, 2003, pp. 257-263, 13, No. 4.

Reyes-Sanchez et al., "External fixation for dynamic correction of severe scoliosis", The Spine Journal, 2005, pp. 418-426, 5, No. 4.

Rinsky et al., "Segmental instrumentation without fusion in children with progressive scoliosis.", Journal of Pediatric Orthopedics, 1985, pp. 687-690, 5, No. 6.

Rode et al., "A simple way to adjust bands under radiologic control", Obesity Surgery, 2006, p. 418, 16, No. 4.

Schmerling et al., "Using the shape recovery of nitinol in the Harrington rod treatment of scoliosis.", Journal of Biomedical Materials Research, 1976, pp. 879-892, 10, No. 6.

Scott et al., "Transgastric, transcolonic and transvaginal cholecystectomy using magnetically anchored instruments.", Sages Annual Scientific Sessions, Poster Abstracts, Apr. 18-22, 2007, p. 511, p. 306.

Sharke, "The machinery of life", Mechanical Engineering Magazine, Feb. 2004, Printed from Internet site Oct. 24, 2007 http://www.memagazine.org/contents/current/features/moflife/moflife.html.

Shiha et al., "Ilizarov gradual correction of genu varum deformity in adults.", Acta Orthop Belg, 2009, pp. 784-791, 75, No. 6.

Simpson et al., "Femoral lengthening with the intramedullary skeletal kinetic distractor.", Journal of Bone and Joint Surgery, 2009, pp. 955-961, 91-B, No. 7.

Smith, "The use of growth-sparing instrumentation in pediatric spinal deformity.", Orthopedic Clinics of North America, 2007, pp. 547-552, 38, No. 4.

Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).

Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).

Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.

Sun et al., "Masticatory mechanics of a mandibular distraction osteogenesis site: Interfragmentary micromovement.", Bone, 2007, pp. 188-196, 41, No. 2.

Synthes Spine, "VEPTR II. Vertical Expandable Prosthetic Titanium Rib II: Technique Guide.", 2008, 40 pgs.

Synthes Spine, "VEPTR Vertical Expandable Prosthetic Titanium Rib, Patient Guide.", 2005, 26 pgs.

Takaso et al., "New remote-controlled growing-rod spinal instrumentation possibly applicable for scoliosis in young children.", Journal of Orthopaedic Science, 1998, pp. 336-340, 3, No. 6.

Teli et al., "Measurement of forces generated during distraction of growing rods.", Journal of Children's Orthopaedics, 2007, pp. 257-258, 1, No. 4.

Tello, "Harrington instrumentation without arthrodesis and consecutive distraction program for young children with severe spinal deformities: Experience and technical details.", The Orthopedic Clinics of North America, 1994, pp. 333-351, 25, No. 2.

Thaller et al., "Limb lengthening with fully implantable magnetically actuated mechanical nails (PHENIX®)—Preliminary results.", Injury, 2014 (E-published Oct. 28, 2013), pp. S60-S65, 45.

Thompson et al., "Early onset scoliosis: Future directions", 2007, J Bone Joint Surg Am, pp. 163-166, 89-A, Suppl 1.

Thompson et al., "Growing rod techniques in early-onset scoliosis", Journal of Pediatric Orthopedics, 2007, pp. 354-361, 27, No. 3.

Thonse et al., "Limb lengthening with a fully implantable, telescopic, intramedullary nail.", Operative Techniques in Orthopedics, 2005, pp. 355-362, 15, No. 4.

Trias et al., "Dynamic loads experienced in correction of idiopathic scoliosis using two types of Harrington rods.", Spine, 1979, pp. 228-235, 4, No. 3.

Verkerke et al., "An extendable modular endoprosthetic system for bone tumor management in the leg", Journal of Biomedical Engineering, 1990, pp. 91-96, 12, No. 2.

Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.

Verkerke et al., "Development and test of an extendable endoprosthesis for bone reconstruction in the leg.", The International Journal of Artificial Organs, 1994, pp. 155-162, 17, No. 3.

Weiner et al., "Initial clinical experience with telemetrically adjustable gastric banding", Surgical Technology International, 2005, pp. 63-69, 15.

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.

White, III et al., "The clinical biomechanics of scoliosis.", Clinical Orthopaedics and Related Research, 1976, pp. 100-112, 118.

Yonnet, "A new type of permanent magnet coupling.", IEEE Transactions on Magnetics, 1981, pp. 2991-2993, 17, No. 6.

Yonnet, "Passive magnetic bearings with permanent magnets.", IEEE Transactions on Magnetics, 1978, pp. 803-805, 14, No. 5.

(56) References Cited

OTHER PUBLICATIONS

Zheng et al., "Force and torque characteristics for magnetically driven blood pump.", Journal of Magnetism and Magnetic Materials, 2002, pp. 292-302, 241, No. 2.

* cited by examiner

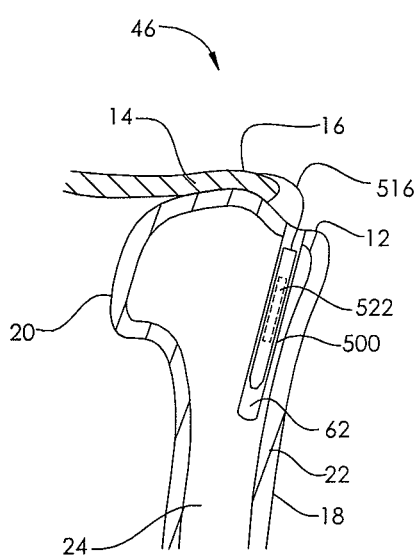 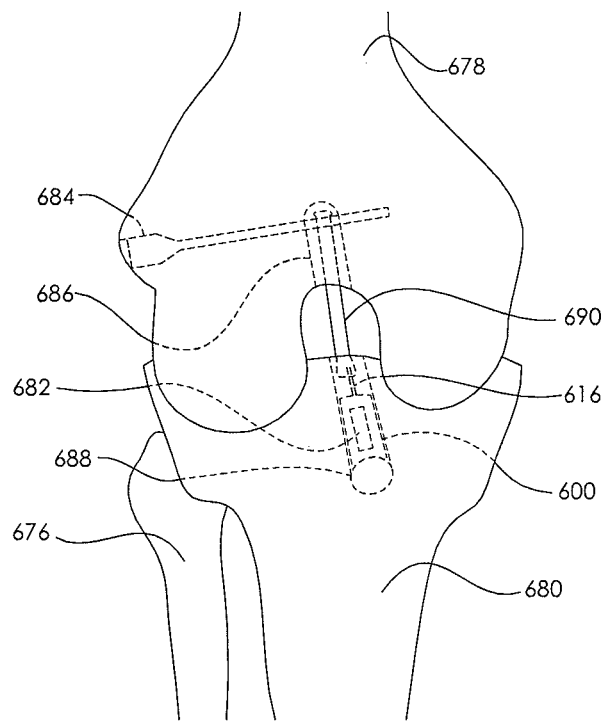
FIG. 11
FIG. 12

NONINVASIVELY ADJUSTABLE SUTURE ANCHORS

CROSS REFERENCE TO RELATED APPLICATIONS

The present application is a continuation of U.S. application Ser. No. 17/374,350, filed Jul. 13, 2021, which is a divisional of U.S. application Ser. No. 16/257,526, filed Jan. 25, 2019 (now U.S. Pat. No. 11,090,039), which is a continuation of U.S. application Ser. No. 14/447,391, filed Jul. 30, 2014 (now U.S. Pat. No. 10,226,242), which in turn claims the benefit of U.S. Provisional Application No. 61/860,668, filed Jul. 31, 2013, each of which is hereby incorporated by reference in its entirety under 37 CFR 1.57.

TECHNICAL FIELD

The field of the invention generally relates to medical devices for attaching soft tissue to bone.

BACKGROUND

In many common surgical techniques, soft tissue (muscle, tendon, ligament) is secured to the bone using a variety of types of tissue anchors. In most of these surgeries, it is important that that the connection between the soft tissue and the bone remain consistent, without significant degradation after surgery and recovery, both short term and long term. One common method of securing soft tissue to bone is with a suture anchor, which is sutured or otherwise attached to the particular portion of soft tissue and then anchored to the bone. The anchoring to the bone may be achieved by a threaded screw, or several other types of securement.

One of the common complications of many of these surgical techniques is for the connection between the soft tissue and the bone to degrade. For example, the healing of the tissue may cause the tensile force at which the soft tissue is secured to the bone to increase or decrease. Also, the length of the connection may increase or decrease, creating such effects as too much joint motion, too little joint motion, hyperextension, and of course fatigue and pain. Laxity of a suture is a common occurrence, and can increase the variance in the final tension in the connection of the soft tissue to the bone.

Rotator cuff injury is one of the most common ailments of the shoulder. The rotator cuff is a group of muscles and tendons that stabilize the shoulder joint. Many of the injuries to the rotator cuff are able to be treated without surgery, for example, certain cases of tendonitis and other traumatic injuries. Often, the injury to the rotator cuff involves the tearing of the tendons that attach one or more of the rotator cuff muscles to the humerus (upper arm) bone. Active patients who have substantial or complete tears of one of more portions of the rotator cuff are often treated by rotator cuff surgery. Rotator cuff tears are sometimes classified as small (<1 cm), medium (1 cm to 3 cm), large (3 cm to 5 cm), and massive (>5 cm). They are also characterized by shape, such as transverse, L-shaped, linear, crescent, and triangular. Rotator cuff surgery may be performed as an open surgery, a mini-open surgery (wherein the deltoid muscle need not be detached during surgery), or an arthroscopic surgery. Many different suture techniques are used, each attempting to improve upon strength, stability, safety and procedural speed and invasiveness. In certain groups of patients, postoperative stiffness develops. This may happen in more than 8% of patient under the age of 50, and in more than 15% of patients who also have either calcific tendonitis or adhesive capsulitis. Many patients with postoperative stiffness choose to undergo subsequent arthrosopic procedures to remove or remodel scar tissue. Re-tears are also somewhat common after the recovery following the initial rotator cuff surgery, with reported rates between 4% to 26%.

Anterior cruciate ligament (ACL) injury is common in athletes in a variety of sports, especially in contact sports, with the ACL. ACL reconstruction surgery is often performed after tear or rupture of the ACL, and usually includes the removal of the damaged ligament and replacement with a graft. The graft may be an autograft (a portion of the patient's own patellar tendon or hamstring) or an allograft (cadaveric patellar tendon, anterior tibialis tendon, or Achilles tendon). This surgery is commonly performed arthroscopically, with the graft inserted into tunnels created in the tibia and femur, and then secured to these bones with tissue anchors. Post-recovery, some ACL reconstruction patients have persistent loss in range of motion, in either flexion or extension, which may be due to imprecise placement of the graft during the initial surgery or the healing process itself. A classification system has been proposed that includes four different grades: Type 1: less than a 10° loss of extension with normal flexion, Type 2: more than a 10° loss of extension with normal flexion, Type 3: more than a 10° loss of extension with a flexion deficit of greater than 25°, and Type 4: more than a 20° loss of extension with a flexion deficit greater than 30°. Some of these patients are able to improve through rehabilitation, but others require an additional surgical procedure.

Despite the wide variety of available devices for anchoring soft tissue (e.g. tendon) to bone, there remains a need for an implant which can be adjusted post-operatively to increase or decrease tension without the need for additional surgical intervention.

SUMMARY

In a first embodiment of the invention, an adjustable implant system includes a bone anchor having a first end and a second end, and including a bone engagement surface adjacent the first end, the bone anchor further comprising a housing extending between the first end and the second end. The adjustable implant system further includes a driving element carried within the housing and configured for noninvasive actuation, wherein the driving element is coupled to an adjustment component, the adjustment component configured for coupling to a flexible elongate tension member capable of engaging soft tissue of a patient, wherein noninvasive actuation of the driving element causes the adjustment component to change the amount of tension on the flexible elongate tension member. The adjustable implant system further includes an external adjustment device comprising at least one energy transferring component and configured to be placed on or adjacent the skin of the patient, and wherein the at least one energy transferring component of the external adjustment device is configured to energize the driving element inside the housing of the adjustable implant.

In another embodiment of the invention, a method of treating a patient includes the steps of providing a tensioning device having a connector for connection to soft tissue, and a drive for drawing the connector in the direction of the tensioning device, inserting the tensioning device into a bone, and connecting the connector to soft tissue, wherein the tensioning device is configured to draw the connector in the direction of the tensioning device in response to a wireless signal.

In another embodiment of the invention, a method of treating a patient includes: providing a tensioning device having: a connector configured to couple to a soft tissue, and an adjustable anchor configured to couple to the connector and to couple to a bone, wherein the adjustable anchor comprises: a first end and a second end; a housing extending between the first end and the second end; and an adjustable component disposed within the housing; inserting the second end of the adjustable anchor into the bone; connecting the connector to the soft tissue; coupling the connector to the adjustable anchor; and adjusting a tension on the connector by rotating the adjustable component within the housing in response to a wireless signal.

In another embodiment of the invention, a device includes: a connector configured to couple to a soft tissue, and an adjustable anchor configured to couple to the connector and couple to a bone, the adjustable anchor having: a first end and a second end; a housing extending between the first end and the second end; and an adjustable component disposed within the housing, wherein the adjustable component comprises: a shaft; a hollow, radially poled magnet disposed about the shaft; and a magnet housing disposed about and radially affixed to the hollow, radially poled magnet, the magnet housing having an external thread along a portion of an axial extent thereof.

In another embodiment of the invention, a tensioning device includes: a connector configured to couple to a soft tissue, and an adjustable anchor configured to couple to the connector and couple to a bone, the adjustable anchor having: a first end and a second end; a housing extending between the first end and the second end; and an adjustable component disposed within the housing, wherein the adjustable component comprises: a cylindrical magnet configured to rotate within the housing; and a spool coupled to the cylindrical magnet, wherein the spool is configured to rotate within a longitudinal cavity of the housing upon actuation by the cylindrical magnet, and wherein the connector is partially wound on the spool.

All examples and features mentioned below can be combined in any technically possible way.

In certain cases, the bone is a humerus, a femur, or a tibia, and wherein the soft tissue is a rotator cuff tendon, an anterior cruciate ligament, or a replacement for a ligament.

In some cases, the method further includes: adjusting the tension by axially translating the adjustable component within a longitudinal cavity in the housing, wherein the adjustable component comprises: a shaft; a hollow, radially poled magnet disposed about the shaft; and a magnet housing disposed about and radially affixed to the hollow, radially poled magnet, the magnet housing having an external thread along a portion of an axial extent thereof.

In some cases, the adjustable component further comprises an eyelet disposed at the first end thereof, and the connector comprises a suture; and the method further comprises coupling the suture to the eyelet by threading the suture through the eyelet and securing the suture to the eyelet.

In some cases, the adjustable component is rotationally fixed relative to the housing.

In some cases, the method further includes: threadingly engaging an internal thread of the longitudinal cavity of the housing with the external thread of the magnet housing, and applying to the patient a magnetic field configured to move in a first rotational direction or a second rotational direction opposite the first rotational direction, thereby causing the hollow, radially poled magnet and the magnet housing to rotate in the second rotational direction or the first rotational direction, respectively, and further causing the adjustable component to axially translate relative to the housing, wherein the magnetic field is applied non-invasively and externally relative to the patient.

In some cases, applying the magnetic field in the first rotational direction shortens an effective length of the connector and increases tension thereon, and applying the magnetic field in the second rotational direction lengthens the effective length of the connector and decreases tension thereon.

In some cases, the method further includes non-invasively adjusting the tension on the connector relative to the adjustable anchor while the patient is awake and mobile.

In some cases, the adjustable component comprises: a cylindrical magnet configured to rotate within the housing; and a spool coupled to the cylindrical magnet, wherein the spool is configured to rotate within the longitudinal cavity of the housing upon actuation by the cylindrical magnet, and wherein the connector is partially wound on the spool.

In some cases, the method further includes: applying to the patient a magnetic field configured to move in either a first rotational direction or a second rotational direction opposite the first rotational direction, wherein applying the magnetic field in the first rotational direction causes the cylindrical magnet and the spool to rotate in the first rotational direction, thereby increasing the tension on the connector relative to the adjustable anchor, and applying the magnetic field in the second rotational direction causes the cylindrical magnet and the spool to rotate in the second rotational direction, thereby decreasing the tension on the connector, and wherein the magnetic field is applied non-invasively and externally relative to the patient.

In some cases, the method further includes: causing the cylindrical magnet to rotate at a first rotational speed, and the spool to rotate at a second rotational speed in a same direction, wherein the second rotational speed is slower than the first rotational speed.

In some cases, the method further includes: prior to the inserting, preparing a first hole into the bone, the first hole being configured to receive the adjustable anchor, and preparing a second hole into the bone, wherein the second hole extends at an angle relative to the first hole and is in communication with the first hole, such that the second hole is configured to receive a portion of the connector therethrough.

In some cases, the adjustable component further comprises an eyelet disposed at the first end thereof, and the connector comprises a suture, wherein the suture is sized to threadingly couple to the eyelet.

In some cases, the adjustable component is rotationally fixed relative to the housing.

In some cases, the adjustable component is disposed within a longitudinal cavity in the housing, and tension on the connector is adjustable by rotating the adjustable component within the housing, thereby axially translating the adjustable component within the longitudinal cavity in the housing.

In some cases, the external thread of the magnet housing threadingly engages an internal thread of the longitudinal cavity of the housing.

In some cases, a method of adjusting the device includes adjusting a tension on the connector by rotating the adjustable component within the housing in response to a wireless signal.

In some cases, the housing includes an externally threaded portion configured to engage cortical bone.

Two or more features described in this disclosure, including those described in this summary section, may be combined to form implementations not specifically described herein.

The details of one or more implementations are set forth in the accompanying drawings and the description below. Other features, objects and benefits will be apparent from the description and drawings, and from the claims.

BRIEF DESCRIPTION OF THE DRAWINGS

FIG. 11 illustrates a humerus with a hole drilled for placement of an adjustable suture anchor in a rotator cuff patient.

FIG. 12 illustrates a tibia with a hole drilled for placement of an adjustable suture anchor in an anterior cruciate ligament patient.

DETAILED DESCRIPTION

Figure 1:
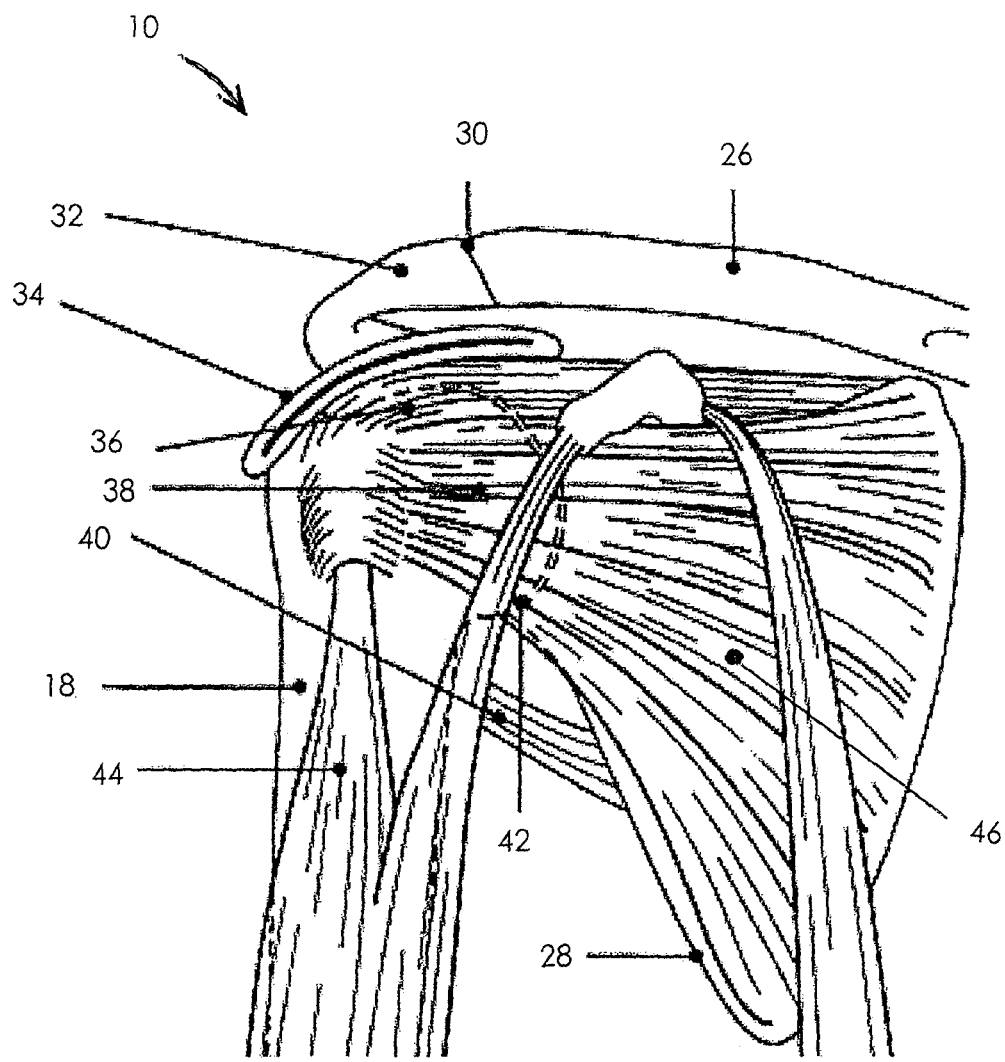
FIG. 1 illustrates the human shoulder.
Figure 2:
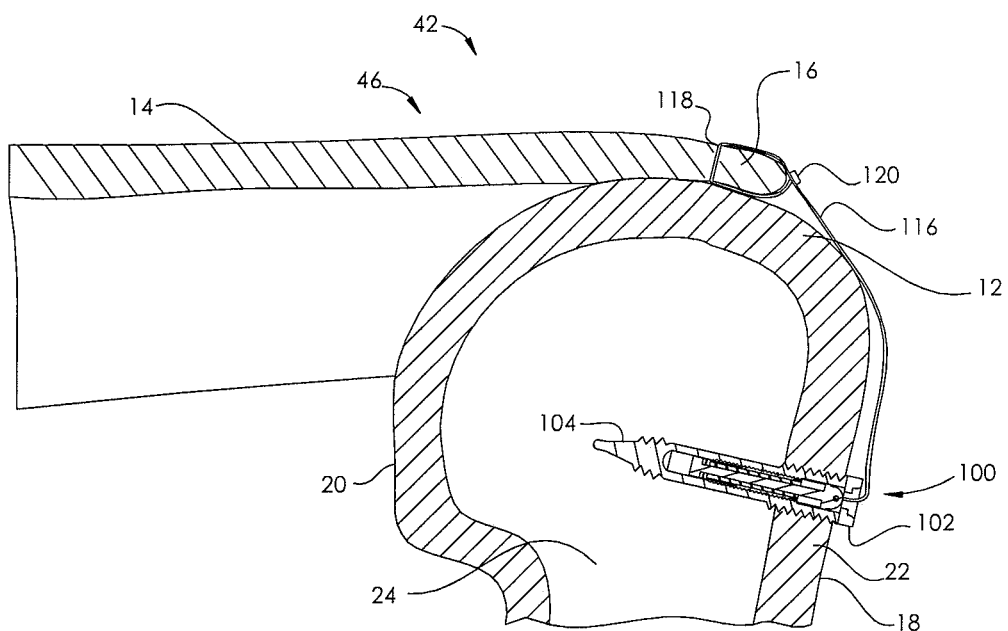
FIG. 2 illustrates a cross-section of an embodiment of an adjustable suture anchor secured in the humerus of a rotator cuff surgery patient.

FIG. 1 illustrates an anatomical view of a human shoulder 10, which includes the following bones: scapula 28, clavicle 26 and humerus 18 The glenohumeral joint 42 (or shoulder joint) is an articulation between the scapula 28 and the head 20 of the humerus 18, the head 20 visible in a cross-sectional view in FIG. 2. The acromion 32 is a bony process on the scapula 28 which articulates with the clavicle 26 at the acromioclavicular joint 30. There is very little interface between the humerus 18 and the scapula 28 in the glenohumeral joint 42 making it the most mobile joint in the human body. The rotator cuff 46 is a group of muscles and their respective tendons which serve to stabilize the shoulder 10, including the supraspinatus 36, infraspinatus (not visible in FIG. 1), subscapularis 38, and teres minor 40. All four of these muscles arise from different portions of the scapula 28 and attach via their respective tendons to either the greater tubercle 12 of the humerus 18, which is lateral to the humeral head 20 or the lesser tubercle (not shown). Also shown in FIG. 1 is the bursa 34, a fluid-filled sac which cushions the bones, muscles and tendons of the glenohumeral joint 42. Additionally, the biceps muscle 44 is shown for perspective purposes.

Figures 3, 4:
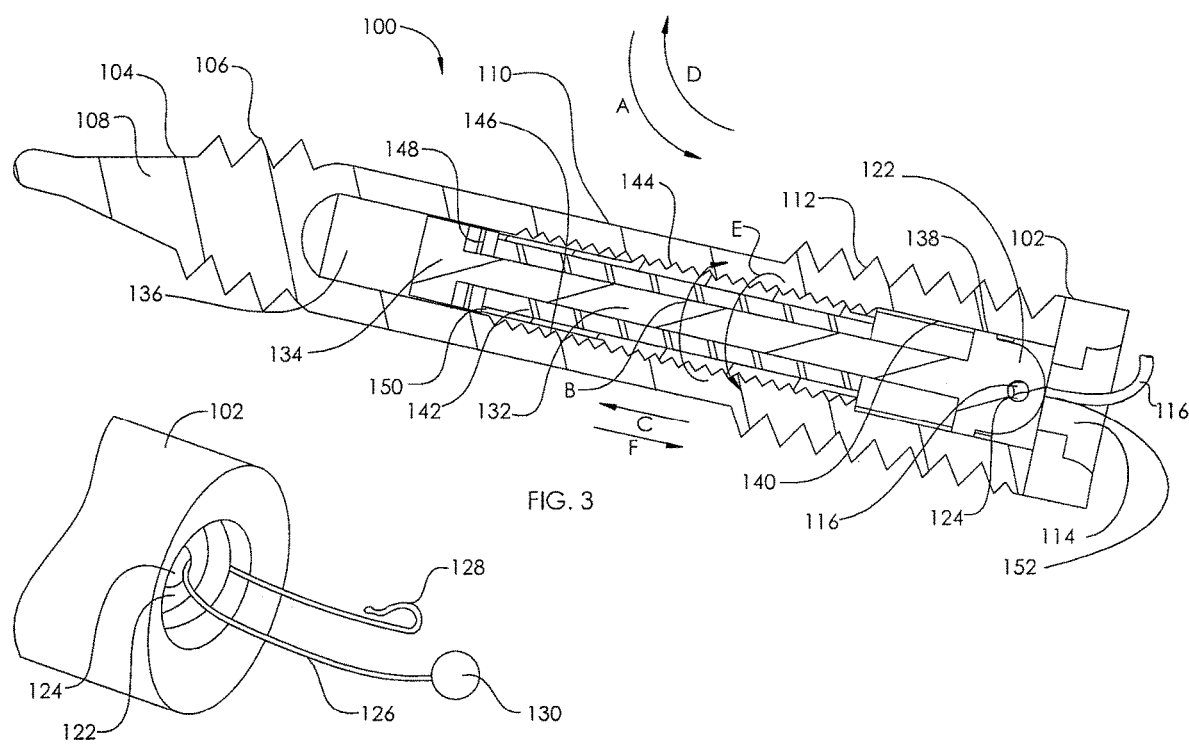
FIG. 3 illustrates a detailed cross-sectional view of the adjustable suture anchor of FIG. 2.
FIG. 4 illustrates a first end of the adjustable suture anchor supplied with a threading tool.

A simplified cross-sectional view of the shoulder 10 is shown in FIG. 2, with an embodiment of an adjustable suture anchor 100 implanted within the shoulder 10. The adjustable suture anchor 100 has a first end 102 and a second end 104, the second end 104 configured for insertion through cancellous bone 24 and the first end 102 configured for securing in the cortical bone 22 of the humerus 18. In FIG. 3 detail of the second end 104 shows a tapered thread 106 and a tapered tip 108, which can aid in driving the adjustable suture anchor 100 through the humerus 18. Alternatively, an initial hole may be reamed in the cortical bone 22 and cancellous bone 24 to aid in the insertion of the adjustable suture anchor 100. A housing 110 extends between the first end 102 and second end 104 of the adjustable suture anchor 100. At the first end 102, a threaded portion 112 is provided which allows a secure interface with the cortical bone 22. The threaded portion 112 may be of a single major diameter (for example with a minor diameter that increases towards the first end), or the major diameter may vary from smaller to larger as it approaches the first end 102. The threaded portion 112 may be provided with cutting threads, in order to better create the interface with the cortical bone 22. A keyed cavity 114 is provided in the first end 102 for interfacing with a driving tool. The shapes of both the driving tool and the keyed cavity 114 may be hexagonal, cross-shaped, star-shaped or a number of other keyed shapes that allow a maximal torque in securing the adjustable suture anchor 100 into the humerus 18.

A simplified rotator cuff 46 is represented in FIG. 2 by a muscle 14 and its tendon 16, in cross-section. In this embodiment of the adjustable suture anchor 100, a suture 116 is secured to the tendon 16 through at least one puncture 118. The suture 116 is held in place with one or more knots 120, which may comprise a number of different knot types. Any of the possible suturing techniques are envisioned, including: single-row technique, double-row techniques, diamond, mattress double anchor, or modified mattress double anchor.

The adjustable suture anchor 100 contains within its housing 110 an adjustable component 122 having an eyelet 124. The eyelet 124 is configured for securing an end of the suture 116. As shown in FIG. 4, the adjustable suture anchor 100 is supplied with a threading tool 126, which can be used to aid the placement of the suture 116 through the eyelet 124 of the adjustable component 122. The suture 116 is looped through or tied to a hook 128 in the threading tool 126, and then the threading tool 126 is pulled from gripping structure 130 at the opposite end of the threading tool 126 from the hook 128. The suture 116 is pulled through the eyelet 124 of the adjustable component 122 and tied or otherwise secured in place. The suture 116 is tied with the desired amount of tension.

The adjustable component 122 of the adjustable suture anchor 100 further includes a shaft 132 and a base 134 at the opposite end of the shaft 132 from the eyelet 124. The adjustable component 122 is configured to be axially movable within a longitudinal cavity 136 of the housing 110. Fins 138 are slidable within longitudinal grooves 140 in the longitudinal cavity 136 of the housing 110, thus inhibiting the rotation of the adjustable component 122 in relation to the housing 110. The hollow magnet 142 is radially poled, and is bonded within a threaded magnet housing 144. The threaded magnet housing 144 threadingly engages an internal thread 146 of the housing 110. A thrust bearing 148 is disposed between the base 134 of the adjustable component 122 and a first end 150 of the threaded magnet housing 144. If it is desired during or particularly after surgery to tighten the tension on the suture 116, a moving magnetic field is applied externally to the patient in a first rotational direction A, causing the hollow magnet 142 and threaded magnet housing 144 to spin in a second rotational direction B. Because it is secured to the hollow magnet 142, the threaded magnet housing 144 therefore turns within the internal thread 146 of the housing 110, actuating it in a first axial direction C. As the first end 150 of the threaded magnet housing 144 pushes against the thrust bearing 148 and the base 134 of the adjustable component 122, the adjustable component 122 is moved in the first axial direction C. This shortens the effective length of the suture 116, and thus increases its tensile force, which is the force it applies to the tendon 16. This ability to adjust the tension on the suture 16 non-invasively on an awake, mobile patient, make it possible to assure the ideal state of the shoulder 10 during the healing process. To isolate the longitudinal cavity 136 of the housing (and its contents) from body fluids, a seal 152 is carried near the first end 102 of the adjustable suture anchor 100. The suture 116 is able to move within this seal 152 (o-ring or slit diaphragm) without causing any significant material to enter the longitudinal cavity 136. If the tension on the suture 116 is higher than desired, a moving magnetic field is applied externally to the patient in a rotational direction D (opposite A), causing the hollow magnet 142 and threaded magnet housing 144 to spin in a rotational direction E (opposite B). This moves the adjustable component in an axial direction F (opposite C). The tension on the suture 116 is thus lowered.

Figure 5:
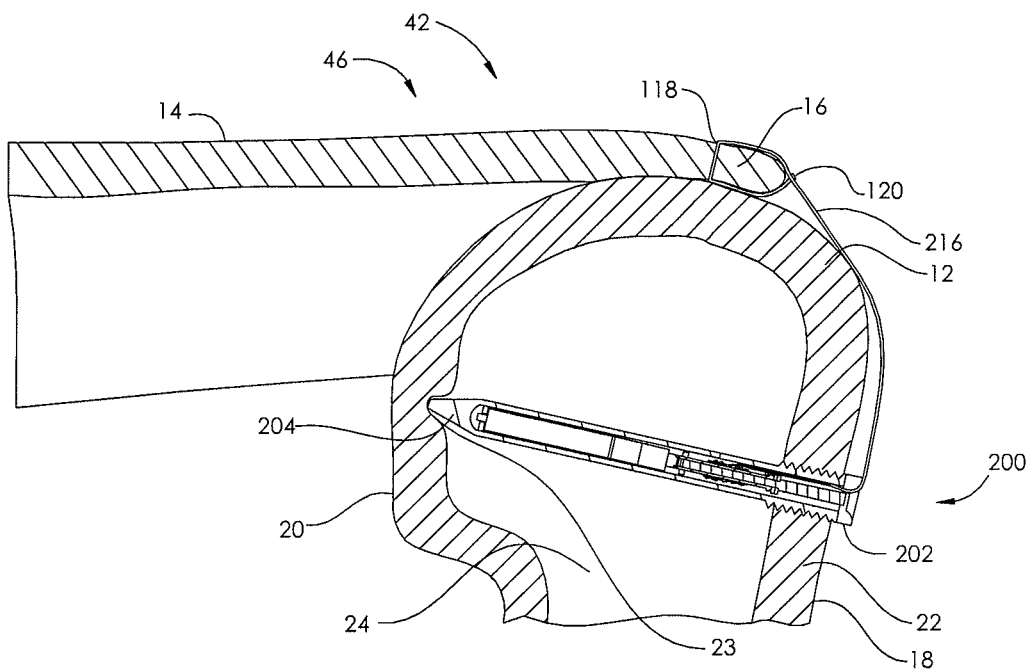
FIG. 5 illustrates a cross-section of an embodiment of an adjustable suture anchor secured in the humerus of a rotator cuff surgery patient.
Figure 6:
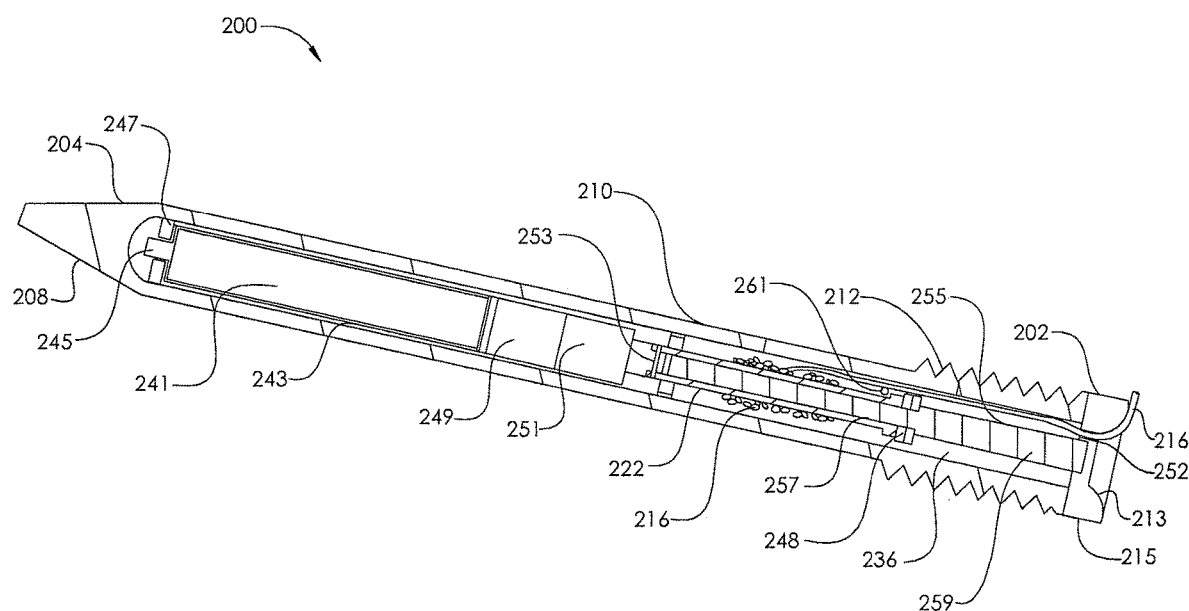
FIG. 6 illustrates a detailed cross-section view of the adjustable suture anchor of FIG. 5.

Turning now to FIG. 5, a different embodiment of an adjustable suture anchor 200 is depicted in its implanted configuration within the humerus 18. The adjustable suture anchor 200 has a first end 202 and a second end 204. As seen in more detail in FIG. 6, the second end 204 includes a tapered tip 208, to aid in insertion through the cancellous bone 24. A pilot hole may be drilled through the cortical bone 24 and the cancellous bone 24, and an additional pocket 23 may be drilled, into which the tapered tip 208 may reside, for increased stability. A threaded portion 212 is provided adjacent the first end 202 of the adjustable suture anchor 200 for engaging with the cortical bone 24. A keyed outer surface 215, having for example a hexagonal shape, is provided for tightening the adjustable suture anchor into humerus 18. In this embodiment, suture 216 extends from a longitudinal cavity 236 within a housing 210 of the adjustable suture anchor. The suture 216 is partially wound on a spool 222, which is rotatable within the longitudinal cavity 236. The suture 216 can slide through a seal 252, which protects the longitudinal cavity 236 from body fluids. The first end 202 of the adjustable suture anchor 200 includes a radiused surface 213, which allows the suture 216 to be slid over it without fraying. A rotatable cylindrical radially-poled magnet 241 bonded within a magnet housing 243 having a pin 245. The magnet housing 243 is constrained axially within the longitudinal cavity 236. The pin 245 turns within a radial bearing 247. The magnet housing 243 connects to a first planetary gear stage 249, which connects to a second planetary gear stage 251. The second planetary gear stage 251 is coupled to the spool 222 by a pin 253. After implanting the adjustable suture anchor 200 into the humerus 18, the suture 216 is pulled partially out of the longitudinal cavity 236 and secured to a tendon 16 via a puncture 118. The suture is tied in a knot 120 so that it is at the desired amount of tension.

If at a later time, for example after surgery, the tension on the suture 216 is higher than desired, a moving magnetic field is applied externally to the patient in a first rotational direction, causing the magnet 241 to be turned, and thus the first and second planetary gear stages 249, 251 and spool 222. Because of the gear reduction from the first and second planetary gear stages 249, 251, the spool 222 is turned at a slower rotational speed than the magnet 241, allowing precision adjustment of the tension in the suture 216. The gearing also allows the desired tension to be achievable without an undesirably large applied moving magnetic field, for example a field that is above International Commission on Non-Ionizing Radiation Protection (ICNIRP) guidelines for current density in body tissues and fluids, for example 0.04 Amperes/m2 or less. As the spool 222 is turned the suture 216 is pulled into the longitudinal cavity 236 through the seal 252, tightening the tension in the suture 216, and thus on the tendon 16. A stepped post 255 is secured to the first end 202 of the adjustable suture anchor 200. A thrust bearing 248 and the spool 222 are both carried on a small diameter portion 257 of the stepped post 255. When the suture 216 is in tension, the spool 222 is forced against the thrust bearing 248, which in turn is forced against the edge of a large diameter portion 259 of the stepped post 255, thus minimizing the rotational resistance of the spool 222. The suture 216 passes through a guide loop 261 to aid its takeup onto the spool 222. In both the adjustable suture anchor 100 and adjustable suture anchor 200, a pulley may be carried by the first end 102, 202 to serve the function of the radiused surface 213, both in keeping the suture 116, 216 from fraying, and in changing the direction of the of the suture 116, 216 which is in tension.

Figure 7:
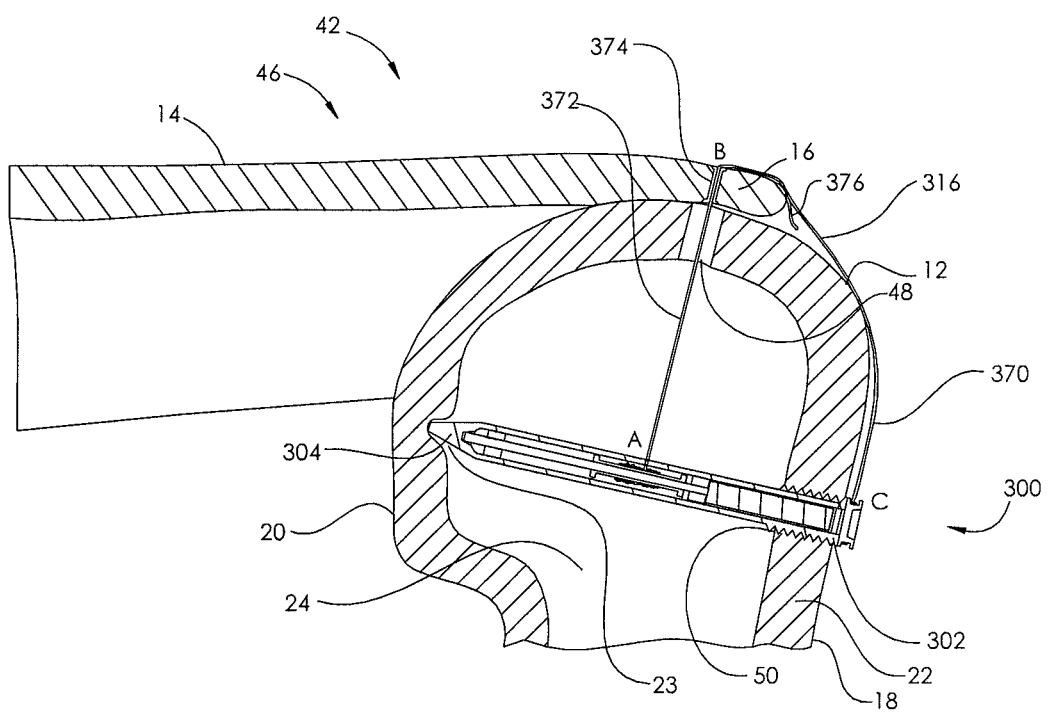
FIG. 7 illustrates a cross-section of an embodiment of an adjustable anchor secured in the humerus of a rotator cuff surgery patient.
Figure 8:
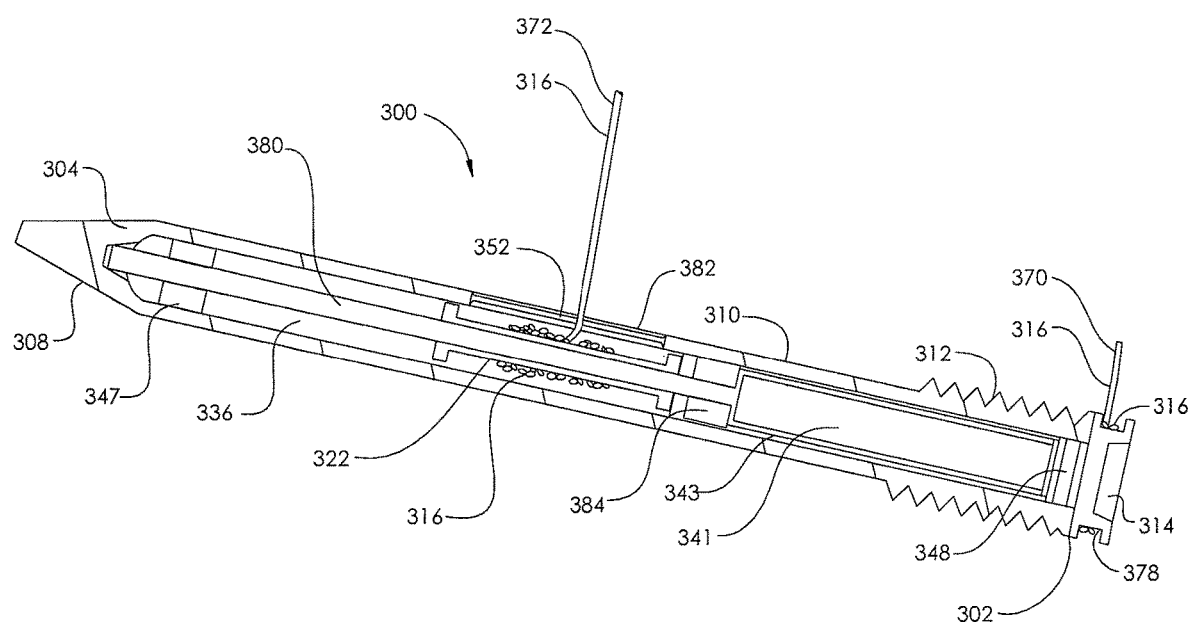
FIG. 8 illustrates a detailed cross-section view of the adjustable suture anchor of FIG. 7.

A different embodiment of an adjustable suture anchor 300 is depicted in FIGS. 7 and 8. In this embodiment, a loop of suture 316 extends from the tendon 16 in an external portion 370 and an internal portion 372. A tunnel 374 through which the suture 316 can slide is made in the tendon 16, so that the length of the loop of suture 316 which extends from point A to point B to point C, can be adjusted, thus adjusting the tension with which the suture 316 holds the tendon 16. A pad 376 of biocompatible material is placed underneath the suture 316 to minimize damage to the tendon as the suture 316 slides over it. A first end 302 of the adjustable suture anchor 300 includes a threaded portion 312 and an external circumferential groove 378, around which external portion 370 of suture 316 can be wrapped and/or tied. A second end 304 of the adjustable suture anchor 300 has a tapered tip 308, which may be used as described in the prior embodiments. Within the longitudinal cavity 336 of the housing 310 of the adjustable suture anchor 300, a cylindrical, radially poled magnet 341 is bonded within a magnet housing 343, which is secured to a rotating shaft 380. The magnet housing 343 and shaft 380 are rotatably held between a radial bearing 347 and a thrust bearing 348. A spool 322 is secured to the shaft 380 so that rotation of magnet 341 causes rotation of the shaft. A spacer 384 is disposed between the spool 322 and the magnet 341 and secured to the housing 310. A seal or diaphragm 352 is carried within an aperture 382 in the lateral wall of the housing 310, allowing the internal portion 372 of the loop of suture 316 to move in and out of the housing 310 of the adjustable suture anchor 300, with the contents of the longitudinal cavity 336 remaining protected from body fluids.

During implantation, two pilot holes are drilled through which through the cortical bone 22 and cancellous bone 24, a first hole 50 extending from point C towards point A. The first hole may even be extended to create an additional pocket 23. A second hole 48 extends from point B towards (and just past) point A. A grasper tool is placed through hole 48, and a suture insertion tool inserts the end of the external portion 370 of the suture 316 through hole 50. The grasper tool grasps the suture 316 and pulls it out through hole 48. The adjustable suture anchor is then inserted and secured inside hole 50, tightening it with a driving tool inserted into a keyed cavity 314. The housing may be oriented so that the aperture 382 extends in a direction towards hole 48. The external portion 370 of the suture 316 is now placed through the tunnel 374 in the tendon 16, and then wrapped and/or tied around the external circumferential groove 378, thus closing the loop in the suture 316. To adjust the tension of the suture 316, a moving magnetic field is applied externally to the patient in a first rotational direction, causing the magnet 341 to turn and the spool 322 to tighten the tension in the suture 316. The moving magnetic field may be applied in an opposite rotational direction in order to loosen the tension in the suture 316.

Figure 9:
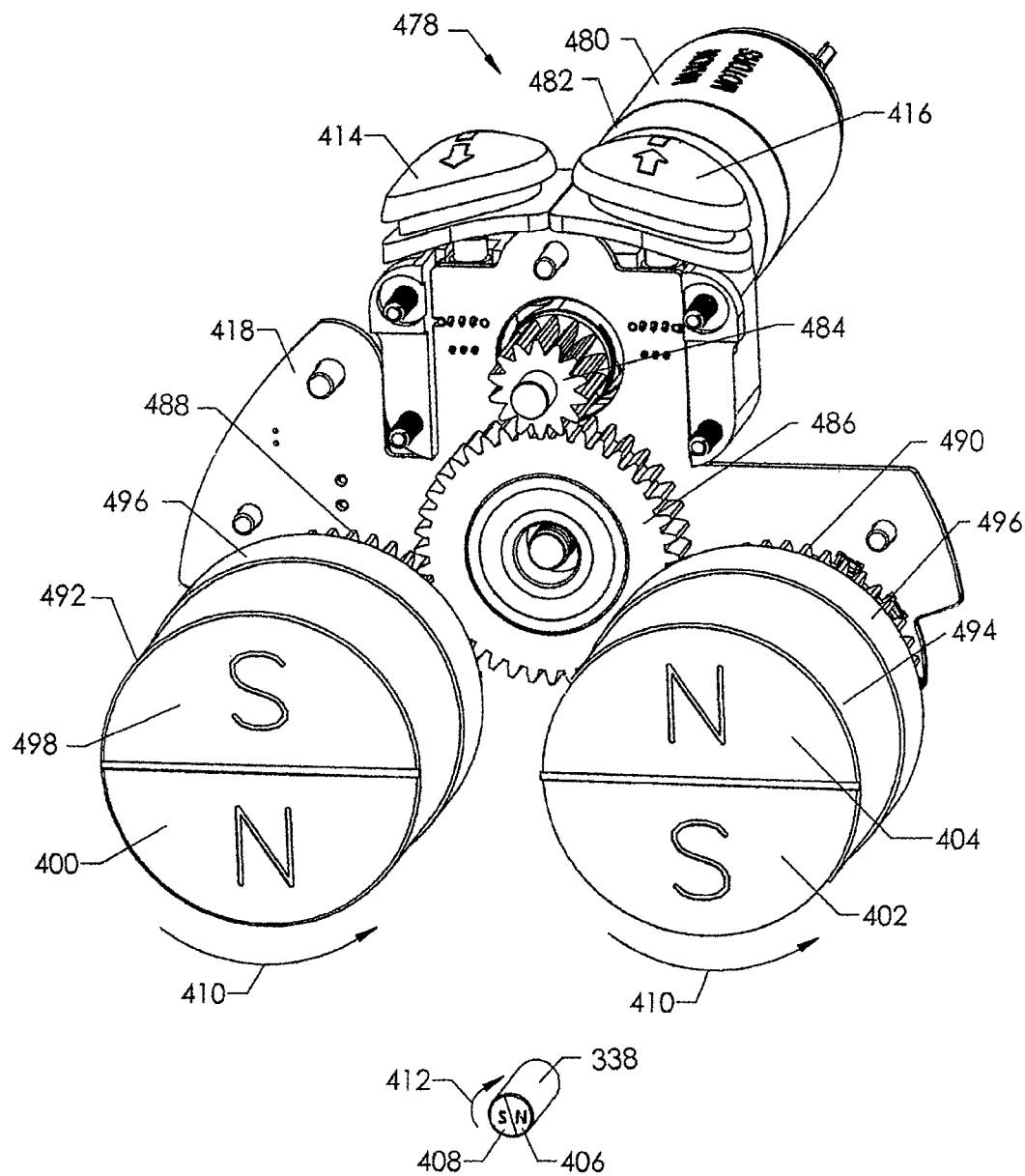
FIG. 9 illustrates internal components of an external adjustment device for non-invasively adjusting an adjustable suture anchor according to one embodiment.
Figure 10:
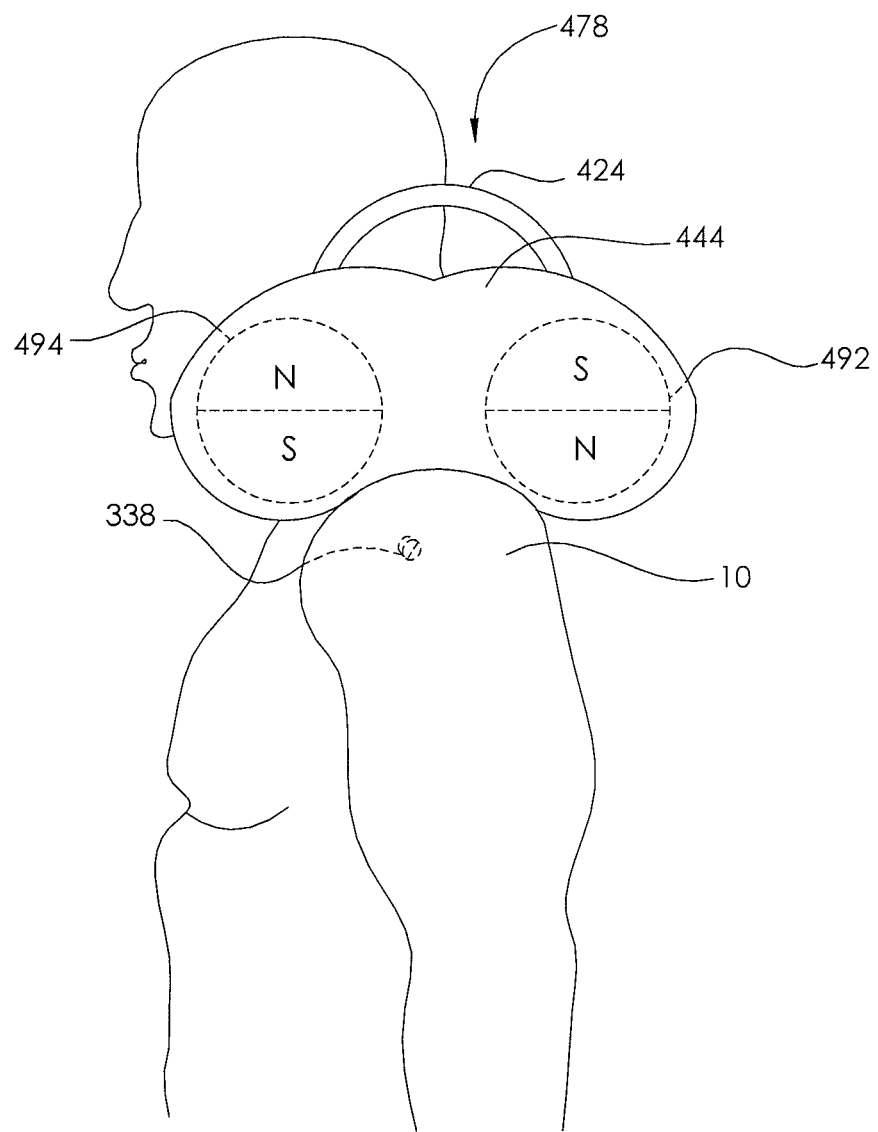
FIG. 10 illustrates an external adjustment device in a configuration for adjusting an adjustable suture anchor implanted within the humerus.

FIGS. 9 and 10 illustrate an external adjustment device 478 configured for applying a moving magnetic field to allow for non-invasive adjustment of the adjustable suture anchor 100, 200, 300 by turning the magnet 142, 241, 341 within the adjustable suture anchor 100, 200, 300. FIG. 9 illustrates the internal components of the external adjustment device 478, and for clear reference, shows a simplified version 338 of the magnet 142, 241, 341 of the adjustable suture anchor 100, 200, 300, without the rest of the assembly. The internal working components of the external adjustment device 478 may, in certain embodiments, be similar to that described in U.S. Patent Application Publication No. 2012/0004494. A motor 480 with a gear box 482 outputs to a motor gear 484. The motor gear 484 engages and turns a central (idler) gear 486, which has the appropriate number of teeth to turn first and second magnet gears 488, 490 at identical rotational speeds. First and second magnets 492, 494 turn in unison with the first and second magnet gears 488, 490, respectively. Each magnet 492, 494 is held within a respective magnet cup 496 (shown partially). An exemplary rotational speed is 60 RPM or less. This speed range may be desired in order to limit the amount of current density induced in the body tissue and fluids, to meet international guidelines or standards. As seen in FIG. 9, the south pole 498 of the first magnet 492 is oriented the same as the north pole 404 of the second magnet 494, and likewise, the first magnet 492 has its north pole 400 oriented the same as the south pole 402 of the second magnet 494. As these two magnets 492, 494 turn synchronously together, they apply a complementary and additive moving magnetic field to the radially-poled, magnet 338, having a north pole 406 and a south pole 408. Magnets having multiple north poles (for example, two) and multiple south poles (for example, two) are also contemplated in each of the devices. As the two magnets 492, 494 turn in a first rotational direction 410 (e.g., counter-clockwise), the magnetic coupling causes the magnet 338 to turn in a second, opposite rotational direction 412 (e.g., clockwise). The rotational direction of the motor 480 is controlled by buttons 414, 416. One or more circuit boards 418 contain control circuitry for both sensing rotation of the magnets 492, 494 and controlling the rotation of the magnets 492, 494.

FIG. 10 shows the external adjustment device 478 for use with an adjustable suture anchor 100, 200, 300 placed in the humerus. The external adjustment device 478 has a first handle 424 attached to a housing 444 for carrying or for steadying the external adjustment device 478, for example, steadying it against a shoulder 10, as in FIG. 10, or against a knee, in the case of an adjustable anchor for anterior cruciate ligament attachment. The external adjustment device 478 includes a control panel including a display (not shown). Control circuitry contained on circuit boards 418 may be used by the surgeon to store important information related to the specific aspects of each particular patient. The external adjustment device 478 may be able to receive and transfer information via an SD card or USB device, or by wireless input. An additional feature is a camera at the portion of the external adjustment device 478 that is placed over the skin. For example, the camera may be located between the first magnet 492 and the second magnet 494. The skin directly over the implanted magnet 338 may be marked with indelible ink. A live image from the camera is then displayed on the display 448 of the control panel 446, allowing the user to place the first and second magnets 492, 494 directly over the area marked on the skin. Crosshairs can be overlayed on the display over the live image, allowing the user to align the mark on the skin between the crosshairs, and thus optimally place the external adjustment device 478.

FIG. 11 illustrates an alternative geometry for creating a hole 62 at the greater tubercule 12 of the humerus 18. An adjustable suture anchor 500 having an adjustable component 522 is implanted in the hole 62 and is capable of adjusting the tension in a suture 516, which is attached to a tendon 16 of a rotator cuff 46. The hole 62 is parallel the axis of the humerus 18, and thus allows for a longer length adjustable suture anchor 500. This makes possible an adjustable suture anchor 500 with more planetary gear sets and allow allows for a greater range of adjustability (length, tension).

Though the adjustable suture anchors 100, 200, 300, 500 as described are adapted for attaching the tendon of the rotator cuff to the humerus, it is conceived that similar suture anchors would be useful for adjusting other soft tissue attachments to bone. Some examples include the anterior cruciate ligament (ACL) in one or both of its attachment point to the bone (femur and/or tibia). FIG. 12 shows a configuration for an adjustable suture anchor 600 for adjusting the tension in a graft 690 for replacing the ACL (for example a portion of the patellar tendon). The graft 690 is secured in a femoral tunnel 686 in a femur 678 with a traditional tissue anchor 684. The tissue anchor 684 may be metallic, or may be of a resorbable material. The adjustable suture anchor 600 is anchored to bone inside a tibial tunnel 688 created in a tibia 680. An adjustable component 682 within the adjustable suture anchor 600 adjusts the tension in a suture 616 which is attached to the graft 690. The diameter of the tissue anchor 684 may be less than about 14 mm, or preferably less than about 12 mm. The length of the femoral tunnel 686 may be on the order of about 25 mm to about 35 mm.

An alternative ligament for which the adjustable suture anchors 100, 200, 300, 500, 600 may be used is the medial collateral ligament (MCL) whose attachment points are the femur 678 and tibia 680. The lateral collateral ligament (LCL), whose attachment points are the femur 678 and fibula 676, may also be adjustably attached by a modified embodiment of the adjustable suture anchor 100, 200, 300, 500, 600. Other tendons and ligaments which may benefit from the adjustability of the adjustable suture anchors 100, 200, 300, 500, 600 include the talo-fibular ligament, the tibial tendon, and the Achilles tendon. Typical ranges of the length of adjustment for the tendon and ligament applications discussed may be typically on the order of less than about 2 cm, or in some embodiments less than about 1 cm.

Other indications for an adjustable connection between soft tissue and bone which may benefit from embodiments of the adjustable suture anchors 100, 200, 300, 500, 600 include adjustable slings attached to the pubic bone, for urinary stress incontinence.

Magnet materials may include rare earth magnets, including Neodymium-Iron-Boron. Rigid components of the adjustable suture anchor may be made from titanium, titanium allows, or other biocompatible materials. In some cases, polyether ether ketone (PEEK) may be an appropriate material. In some cases, at least some components may comprise bioabsorbable materials.

On any of the embodiments presented, it is envisioned that a unidirectional version may be constructed. For example, a ratcheting wheel that allows stepped increases in in the rotational direction which increases the tension on the suture, but does not allow the opposite rotational direction to occur. In addition, any of the embodiments may or may not use gearing, for example to increase the deliverable for or increase the precision.

In addition to a threaded screw attachment to the bone, the bone anchor may comprise an interference fit, for example a tack, a bone adhesive interface, or a staple. Additionally pronged, flanged, snagging, barbed, spiked, tabbed or curved anchors may be secured to the bone. Often, multiple anchors are attached in the same patient.

Though magnetic actuating adjustable implants are presented, other non-invasive systems are considered to be within the scope of the adjustable suture anchors described. For example, the adjustable component may be driven by any of a variety of alternative drives such as an implanted motor which may be powered via inductive coupling, internal battery, or hard wired connection via leads that extend percutaneously but may be detached from the implant and removed following a post-surgical adjustment. The adjustable component may instead be driven by an ultrasonically actuated motor, such as a piezoelectric motor manufactured by Actuated Medical of Bellefonte, Pa. The adjustable component may also be driven by a subcutaneous hydraulic or pneumatic pump which pressurizes fluid through a valve when pressure is placed on the skin of the patient, over the pump interface. The adjustable component may also be driven by an implantable shape-memory driven actuator.

The adjustable suture anchors 100, 200, 300, 500, 600 may be configured so that the magnets and magnet housings may be removed from the adjustable suture anchor assembly, using a small minimally invasive incision, leaving the remained of the adjustable suture anchor 100, 200, 300, 500, 600 in place. For example, if magnetic resonance imaging is prescribed for the patient, the magnet may be temporarily or permanently removed, to allow imaging of the implant area.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The terminology used herein is for the purpose of describing particular embodiments only and is not intended to be limiting of the disclosure. As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups. As used herein, "substantially" refers to largely, for the most part, entirely specified or any slight deviation which provides the same technical benefits of the disclosure.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

We claim:

1. A method of treating a patient, comprising:
providing a tensioning device having:
　a connector configured to couple to a soft tissue, and
　an adjustable anchor configured to couple to the connector and to couple to a bone,
　wherein the adjustable anchor comprises:
　　a first end and a second end;
　　a housing extending between the first end and the second end; and
　　an adjustable component disposed within the housing;
inserting the second end of the adjustable anchor into the bone;
connecting the connector to the soft tissue;
coupling the connector to the adjustable anchor; and
adjusting a tension on the connector by rotating the adjustable component within the housing in response to a wireless signal,
wherein the adjustable component comprises:
　a cylindrical magnet configured to rotate within the housing; and
　a spool coupled to the cylindrical magnet,
　wherein the spool is configured to rotate within the longitudinal cavity of the housing upon actuation by the cylindrical magnet, and wherein the connector is partially wound on the spool.

2. The method of claim 1, wherein the bone is a humerus, a femur, or a tibia, and wherein the soft tissue is a rotator cuff tendon, an anterior cruciate ligament, or a replacement for a ligament.

3. The method of claim 1, further comprising:
adjusting the tension by axially translating the adjustable component within a longitudinal cavity in the housing, wherein the adjustable component comprises:
a shaft;
a hollow, radially poled magnet disposed about the shaft; and
a magnet housing disposed about and radially affixed to the hollow, radially poled magnet, the magnet housing having an external thread along a portion of an axial extent thereof.

4. The method of claim 3, wherein the adjustable component further comprises an eyelet disposed at a first end thereof, and the connector comprises a suture; and
wherein the method further comprises coupling the suture to the eyelet by threading the suture through the eyelet and securing the suture to the eyelet.

5. The method of claim 3, wherein the adjustable component is rotationally fixed relative to the housing.

6. The method of claim 3, further comprising:
threadingly engaging an internal thread of the longitudinal cavity of the housing with the external thread of the magnet housing, and
applying to the patient a magnetic field configured to move in a first rotational direction or a second rotational direction opposite the first rotational direction, thereby causing the hollow, radially poled magnet and the magnet housing to rotate in the second rotational direction or the first rotational direction, respectively, and further causing the adjustable component to axially translate relative to the housing,
wherein the magnetic field is applied non-invasively and externally relative to the patient.

7. The method of claim 6, wherein applying the magnetic field in the first rotational direction shortens an effective length of the connector and increases tension thereon, and applying the magnetic field in the second rotational direction lengthens the effective length of the connector and decreases tension thereon.

8. The method of claim 1, further comprising non-invasively adjusting the tension on the connector relative to the adjustable anchor while the patient is awake and mobile.

9. The method of claim 1, further comprising:
applying to the patient a magnetic field configured to move in either a first rotational direction or a second rotational direction opposite the first rotational direction,
wherein applying the magnetic field in the first rotational direction causes the cylindrical magnet and the spool to rotate in the first rotational direction, thereby increasing the tension on the connector relative to the adjustable anchor, and applying the magnetic field in the second rotational direction causes the cylindrical magnet and the spool to rotate in the second rotational direction, thereby decreasing the tension on the connector, and
wherein the magnetic field is applied non-invasively and externally relative to the patient.

10. The method of claim 9, further comprising:
causing the cylindrical magnet to rotate at a first rotational speed, and the spool to rotate at a second rotational speed in a same direction, wherein the second rotational speed is slower than the first rotational speed.

11. The method of claim 1, further comprising:
prior to the inserting,
preparing a first hole into the bone, the first hole being configured to receive the adjustable anchor, and
preparing a second hole into the bone, wherein the second hole extends at an angle relative to the first hole and is in communication with the first hole, such that the second hole is configured to receive a portion of the connector therethrough.

* * * * *